US006468539B1

(12) United States Patent
Cohen et al.

(10) Patent No.: US 6,468,539 B1
(45) Date of Patent: Oct. 22, 2002

(54) PROTEIN TARGETING INTO HIV VIRIONS BASED ON HIV-1 VPR FUSION MOLECULES

(75) Inventors: Eric A. Cohen; Dominique Bergeron; Florent Checroune; Xiao-Jian Yao; Gary Pignac-Kobinger, all of Montréal (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/454,156

(22) Filed: Jan. 19, 1999

Related U.S. Application Data

(62) Division of application No. 08/301,915, filed on Sep. 7, 1994, now Pat. No. 5,861,161.

(51) Int. Cl.$^{7}$ ........................................ A61K 39/00

(52) U.S. Cl. .................. 424/192.1; 435/69.7; 530/300; 530/350; 424/188.1; 424/208.1

(58) Field of Search ............................ 435/69.7, 320.1; 530/300, 350; 424/188.1, 192.1, 208.1, 199.1

(56) References Cited

U.S. PATENT DOCUMENTS

| | | | | |
|---|---|---|---|---|
| 5,278,056 A | 1/1994 | Bank et al. | .............. | 435/172.3 |
| 5,650,306 A | 7/1997 | Nabel et al. | | |
| 6,001,985 A | 12/1999 | Kappes et al. | ............. | 536/23.4 |

FOREIGN PATENT DOCUMENTS

| | | |
|---|---|---|
| WO | WO 90/15875 | 12/1990 |
| WO | WO 93/25235 | 12/1993 |
| WO | WO 94/04686 | 3/1994 |
| WO | WO 94/19456 | 9/1994 |
| WO | WO 95/16705 | 6/1995 |

OTHER PUBLICATIONS

Paxton, W., et al., 1993, "Incorporation of Vpr into human immunodeficiency virus type 1 virions: requirement for the p6 region of gag and mutational analysis", J. Virol. 67(12):7229–7237.
Matsuda, Z, et al., 1993, "A virion–specific inhibitory molecule with therapeutic potential for human immunodeficiency virus type 1", Proc. Nat. Acad. Sci. USA 90(8):3544–8.
Kim, Y.W. and T.W. Chang, 1992, "Potential use of immunœonjugates for AIDS therapy", AIDS Res. Human Retrovir. 8(6):1033–8.
Feinberg, M.B. and D. Trono, 1992, "Intracellular immunization: trans–dominant mutants of HIV gene products as tools for the study and interruption of viral replication", AIDS Res. Human Retrovir., 8(6):1013–22.
Bevec et al. (1992) Proc. Natl. Acad. Sci. USA 89:9870–4.
Boeke et al. (1996) Trends Microbiol. 4:421–7.
Checroune et al. (1995) J. AIDS Hum. Retrovirol. 10:1–7.
Cohen et al. (1988) Nature 334:532–4.
Fletcher et al. (1997) EMBO J. 16:5123–38.
Horton et al. (1994) Virol. 199:453.7
IUPAC–IUB Comm. Biochem. Nomencla. (1972) Biochem. 11:1726–32.
Kappes et al. (1993) Virol. 193:222–33.
Kappes et al. (1994) J. Cell. Biochem. 18B:162 (Abst. No. J513).
Kappes et al. (1995) Keystone Symp. Gene Thera. Mol. Med., J. Cell. Biochem. Suppl., p.395.
Kondo et al. (1995) J. Virol. 69:2759–64.
Kondo et al. (1996) J. Virol. 70:159–64.
Lavallee et al. (1994) J. Virol. 68:1926–34.
Levy et al. (1993) Cell 72:541–50.
Lu et al. (1993) J. Virol. 67:6542–50.
Lu et al. (1995) J. Virol. 69:6873–9.
Malim et al. (1992) J. Exp. Med. 176:1197–201.
Myers et al. (1993) Human Retrovir. AIDS, I–II, Los Alamos Natl. Lab., New Mexico, USA.
Park et al. (1996) J. AIDS Hum. Retrovirol. 11:341–50.
Paxton et al. (1993) J. Virol. 67(12):7229–37.
Rocquigny et al. (1997) J. Biol. Chem. 272:30753–9.
Sato et al. (1996) Virol. 220:208–12.
Serio et al. (1997) Proc. Natl. Acad. Sci. USA 94:3346–51.
Wagner et al. (1994) Virol. 200:162–75.
Wills (1989) Nature 340:323–4.
Woffendin et al. (1996) Proc. Natl. Acad. Sci. USA 93:2889–94.
Wu et al. (1994) J. Virol. 68:6161–9.
Wu et al. (1995) J. Virol. 69:3389–98.
Wu et al. (1996) J. Virol. 70:3378–84.
Wu et al. (1997) EMBO J. 16:5113–22.
Yao et al. (1992) J. Virol. 66:5119–26.
Feinberg et al., AIDS Res.Hum. Retro. 8:1013–1022.
Johnson et al. (1993) Science 260:1286–93.
Kim et al. (1992) AIDS Res. Hum. Retro. 8:1033–38.
Kimpton et al. (1992) J. Virol. 66:2232–39.
Levy et al. (1993) Microbio. Rev. 57:183–289.
Matsuda et al. (1993) PNAS USA 90:3544–48.
Morgan et al. (1993) Annu. Rev. Biochem. 62:191–217.
Morgenstern et al. (1990) Nucl. Acids Res. 18:3587–96.
Orkin et al. (1995) Distributed by the National Institutes of Health.
Tristem et al. (1992) EMBO J. 11:3405–12.
Wang et al. (1994) Virol. 200:524–534.
Wu et al. (1995) American Society for Microbio. Abs:30 pp. 60.
Wu et al. (1995) American Society for Microbio. Abs:44 pp. 63.
Yu et al. (1993) J. Virol. 67:4386–90.

*Primary Examiner*—Laurie Scheiner
*Assistant Examiner*—Jeffrey S. Parkin
(74) *Attorney, Agent, or Firm*—Klauber & Jackson

(57) ABSTRACT

The present invention relates to a Vpr protein, a Vpx protein or fragments thereof which permit the development of chimeric molecules that can be specifically targeted into the mature HIV-1 and HIV-2 virions to affect their structural organization and/or functional integrity, thereby resulting in gene therapy for HIV-1 and HIV-2 infections. The present invention also relates to Vpr/Vpx protein Fragments, p6 protein, p6 protein fragment, or functional derivatives thereof which interfere with the native Vpr/Vpx incorporation into HIV-1 and HIV-2 virions. The present invention also relates to treatment of HIV-1 and HIV-2 infections based on the proteins of the present invention.

11 Claims, 13 Drawing Sheets

VPR from HIVLAI

| | | | | | | | | | | | | | | | |
|---|---|---|---|---|---|---|---|---|---|---|---|---|---|---|---|
| Met | Glu | Gln | Ala | Pro | Glu | Asp | Gln | Gly | Pro | Gln | Arg | Glu | Pro | His | Asn |
| 1 | | | | 5 | | | | | 10 | | | | | 15 | |
| Glu | Trp | Thr | Leu | Glu | Leu | Leu | Glu | Glu | Leu | Lys | Asn | Glu | Ala | Val | Arg |
| | | | 20 | | | | | 25 | | | | | 30 | | |
| His | Phe | Pro | Arg | Ile | Trp | Leu | His | Gly | Leu | Gly | Gln | His | Ile | Tyr | Glu |
| | | 35 | | | | | 40 | | | | | 45 | | | |
| Thr | Tyr | Gly | Asp | Thr | Trp | Ala | Gly | Val | Glu | Ala | Ile | Ile | Arg | Ile | Leu |
| | 50 | | | | | 55 | | | | | 60 | | | | |
| Gln | Gln | Leu | Leu | Phe | Ile | His | Phe | Arg | Ile | Gly | Cys | Arg | His | Ser | Arg |
| 65 | | | | | 70 | | | | | 75 | | | | | 80 |
| Ile | Gly | Val | Thr | Gln | Gln | Arg | Arg | Ala | Arg | Asn | Gly | Ala | Ser | Arg | Ser |
| | | | | 85 | | | | | 90 | | | | | 95 | |

VPR from HIV2ROD

| | | | | | | | | | | | | | | | |
|---|---|---|---|---|---|---|---|---|---|---|---|---|---|---|---|
| Met | Ala | Glu | Ala | Pro | Thr | Glu | Leu | Pro | Pro | Val | Asp | Gly | Thr | Pro | Leu |
| 1 | | | | 5 | | | | | 10 | | | | | 15 | |
| Arg | Glu | Pro | Gly | Asp | Glu | Trp | Ile | Ile | Glu | Ile | Leu | Arg | Glu | Ile | Lys |
| | | | 20 | | | | | 25 | | | | | 30 | | |
| Glu | Glu | Ala | Leu | Lys | His | Phe | Asp | Pro | Arg | Leu | Leu | Ile | Ala | Leu | Gly |
| | | 35 | | | | | 40 | | | | | 45 | | | |
| Lys | Tyr | Ile | Tyr | Thr | Arg | His | Gly | Asp | Thr | Leu | Glu | Gly | Ala | Arg | Glu |
| | 50 | | | | | 55 | | | | | 60 | | | | |
| Leu | Ile | Lys | Val | Leu | Gln | Arg | Ala | Leu | Phe | Thr | His | Phe | Arg | Ala | Gly |
| 65 | | | | | 70 | | | | | 75 | | | | | 80 |
| Cys | Gly | His | Ser | Arg | Ile | Gly | Gln | Thr | Arg | Gly | Gly | Asn | Pro | Leu | Ser |
| | | | | 85 | | | | | 90 | | | | | 95 | |
| Ala | Ile | Pro | Thr | Pro | Arg | Asn | Met | Gln | | | | | | | |
| | | | 100 | | | | | 105 | | | | | | | |

VPX from HIV2ROD

| | | | | | | | | | | | | | | | |
|---|---|---|---|---|---|---|---|---|---|---|---|---|---|---|---|
| Met | Thr | Asp | Pro | Arg | Glu | Thr | Val | Pro | Pro | Gly | Asn | Ser | Gly | Glu | Glu |
| 1 | | | | 5 | | | | | 10 | | | | | 15 | |
| Thr | Ile | Gly | Glu | Ala | Phe | Ala | Trp | Leu | Asn | Arg | Thr | Val | Glu | Ala | Ile |
| | | | 20 | | | | | 25 | | | | | 30 | | |
| Asn | Arg | Glu | Ala | Val | Asn | His | Leu | Pro | Arg | Glu | Leu | Ile | Phe | Gln | Val |
| | | 35 | | | | | 40 | | | | | 45 | | | |
| Trp | Gln | Arg | Ser | Trp | Arg | Tyr | Trp | His | Asp | Glu | Gln | Gly | Met | Ser | Glu |
| | 50 | | | | | 55 | | | | | 60 | | | | |
| Ser | Tyr | Thr | Lys | Tyr | Arg | Tyr | Leu | Cys | Ile | Ile | Gln | Lys | Ala | Val | Tyr |
| 65 | | | | | 70 | | | | | 75 | | | | | 80 |
| Met | His | Val | Arg | Lys | Gly | Cys | Thr | Cys | Leu | Gly | Arg | Gly | His | Gly | Pro |
| | | | | 85 | | | | | 90 | | | | | 95 | |
| Gly | Gly | Trp | Arg | Pro | Gly | Pro | Pro | Pro | Pro | Pro | Pro | Pro | Gly | Leu | Val |
| | | | 100 | | | | | 105 | | | | | 110 | | |

FIG. 2

```
              PREDICTED HELIX                    PREDICTED HELIX
MEQAPEDQGPQREPHNEWTLELLEELKNEAVRHFPRIWLHGLGQHIYETYGDTWAGVEAIIRILQQLLFIHFRIGCRHSRIGVTQQRRARNGASRS
         10        20        30        40        50        60        70        80        90
```

HxBRUWT
---------------------------------------------------------------------------------------------

HxBRUA30F
-----------------------------F---------------------------------------------------------------

HxBRUH33I
--------------------------------I------------------------------------------------------------

HxBRUR73S
---------------------------------------------------------------------S-----------------------

HxBRUG75N
-----------------------------------------------------------------------N---------------------

HxBRUVpr76/79
--------------------------------------------------------------------------⌐--
                                                                          ⌐

HxBRUVpr77/79
---------------------------------------------------------------------------⌐--
                                                                           ⌐

HxBH10Vpr72/78
----------------------------------------------------------------------⌐----
                                                                      ⌐

HxBRURE12,13PG
-----------PG--------------------------------------------------------------------------------

HxBRUE25K
------------------------K--------------------------------------------------------------------

HxBRUEA29,30FK
----------------------------FK---------------------------------------------------------------

HxBRUIL63,64KR
-------------------------------------------------------------KR------------------------------

HxBRULI68,70RK
------------------------------------------------------------------RK-------------------------

HxBRUSR79,80ID
-------------------------------------------------------------------------ID------------------

```
                         SEQUENCE LISTING


(1) GENERAL INFORMATION:

   (iii) NUMBER OF SEQUENCES: 5


(2) INFORMATION FOR SEQ ID NO:1:

     (i) SEQUENCE CHARACTERISTICS:
          (A) LENGTH: 96 amino acids
          (B) TYPE: amino acid
          (C) STRANDEDNESS: single
          (D) TOPOLOGY: linear

    (ii) MOLECULE TYPE: protein

   (iii) HYPOTHETICAL: NO

    (xi) SEQUENCE DESCRIPTION: SEQ ID NO:1:

Met Glu Gln Ala Pro Glu Asp Gln Gly Pro Gln Arg Glu Pro His Asn
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80
```

-continued

```
Ile Gly Val Thr Gln Gln Arg Arg Ala Arg Asn Gly Ala Ser Arg Ser
                85                  90                  95
```

(2) INFORMATION FOR SEQ ID NO:2:

(i) SEQUENCE CHARACTERISTICS:
(A) LENGTH: 105 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:2:

```
Met Ala Glu Ala Pro Thr Glu Leu Pro Pro Val Asp Gly Thr Pro Leu
1               5                   10                  15

Arg Glu Pro Gly Asp Glu Trp Ile Ile Glu Ile Leu Arg Glu Ile Lys
            20                  25                  30

Glu Glu Ala Leu Lys His Phe Asp Pro Arg Leu Leu Ile Ala Leu Gly
        35                  40                  45

Lys Tyr Ile Tyr Thr Arg His Gly Asp Thr Leu Glu Gly Ala Arg Glu
    50                  55                  60

Leu Ile Lys Val Leu Gln Arg Ala Leu Phe Thr His Phe Arg Ala Gly
65                  70                  75                  80

Cys Gly His Ser Arg Ile Gly Gln Thr Arg Gly Gly Asn Pro Leu Ser
                85                  90                  95

Ala Ile Pro Thr Pro Arg Asn Met Gln
            100                 105
```

(2) INFORMATION FOR SEQ ID NO:3:

(i) SEQUENCE CHARACTERISTICS:
(A) LENGTH: 112 amino acids
(B) TYPE: amino acid
(C) STRANDEDNESS: single
(D) TOPOLOGY: linear (ii) MOLECULE TYPE: protein (iii) HYPOTHETICAL: NO (xi) SEQUENCE DESCRIPTION: SEQ ID NO:3:

```
Met Thr Asp Pro Arg Glu Thr Val Pro Pro Gly Asn Ser Gly Glu Glu
1               5                   10                  15

Thr Ile Gly Glu Ala Phe Ala Trp Leu Asn Arg Thr Val Glu Ala Ile
            20                  25                  30

Asn Arg Glu Ala Val Asn His Leu Pro Arg Glu Leu Ile Phe Gln Val
        35                  40                  45

Trp Gln Arg Ser Trp Arg Tyr Trp His Asp Glu Gln Gly Met Ser Glu
    50                  55                  60

Ser Tyr Thr Lys Tyr Arg Tyr Leu Cys Ile Ile Gln Lys Ala Val Tyr
65                  70                  75                  80

Met His Val Arg Lys Gly Cys Thr Cys Leu Gly Arg Gly His Gly Pro
                85                  90                  95

Gly Gly Trp Arg Pro Gly Pro Pro Pro Pro Pro Pro Pro Gly Leu Val
            100                 105                 110
```

(2) INFORMATION FOR SEQ ID NO:4:

-continued

```
     (i) SEQUENCE CHARACTERISTICS:
          (A) LENGTH: 72 amino acids
          (B) TYPE: amino acid
          (C) STRANDEDNESS: single
          (D) TOPOLOGY: linear

    (ii) MOLECULE TYPE: protein

   (iii) HYPOTHETICAL: NO

    (xi) SEQUENCE DESCRIPTION: SEQ ID NO:4:

Met Glu Gln Ala Pro Glu Asp Gln Gly Pro Gln Arg Glu Pro His Asn
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe
65                  70


(2) INFORMATION FOR SEQ ID NO:5:

     (i) SEQUENCE CHARACTERISTICS:
          (A) LENGTH: 52 amino acids
          (B) TYPE: amino acid
          (C) STRANDEDNESS: single
          (D) TOPOLOGY: linear

    (ii) MOLECULE TYPE: protein

   (iii) HYPOTHETICAL: NO

    (xi) SEQUENCE DESCRIPTION: SEQ ID NO:5:

Leu Gln Arg Ser Pro Glu Pro Thr Ala Pro Pro Glu Glu Ser Phe Arg
1               5                   10                  15

Ser Gly Val Glu Thr Thr Thr Pro Pro Gln Lys Gln Glu Pro Ile Asp
            20                  25                  30

Lys Glu Leu Tyr Pro Leu Thr Ser Leu Arg Ser Leu Phe Gly Asn Asp
        35                  40                  45

Pro Ser Ser Gln
    50
```

PROTEIN TARGETING INTO HIV VIRIONS BASED ON HIV-1 VPR FUSION MOLECULES

CROSS REFERENCE TO RELATED APPLICATION

This Application is a Division, of copending application Ser. No. 08/301,915, filed Sep. 7, 1994, now U.S. Pat. No. 5,861,161 the disclosure of which is incorporated herein by reference in its entirety. Applicant claims the benefits of this application under 35 U.S.C. §120.

BACKGROUND OF THE INVENTION (a) Field of the Invention

The invention relates to two different approaches using the Vpr/Vpx protein or p6 protein for treatment of HIV-1 and HIV-2 infections.

(b) Description of Prior Art

Acquired Immune Deficiency Syndrome (AIDS) is a slow degenerative disease of the immune and nervous systems caused by the Human Immunodeficiency Virus (HIV). The life cycle of HIV lies at the heart of the AIDS pandemic. The spread of the disease is primarily determined by the infectious properties of this virus. Progressive lethal degeneration of the immune and central nervous systems results from long term chronic replication of this virus.

HIV belongs to a unique virus family, the retroviridae, a group of small, enveloped, positive stranded, RNA viruses (Lavallée et al., 1994, J. Virol, 68:1926–1934; International Patent Application No. WO 90/158,75 on Dec. 27, 1990 in the name of DANA FARBER CANCER INSTITUTE). These viruses code for an enzyme, the reverse transcriptase, which enables them to replicate their RNA genome through a DNA intermediate. Simple retroviruses Contain three, contiguous reading frames coding for the gag, pol and env genes, which constitute their structural and enzymatic repertoire, all packaged in the progeny virion. The gag and env genes encode the core nucleocapsids proteins and the membrane glycoproteins of the virus, respectively, whereas the pol gene gives rise to the reverse transcriptase and other enzymatic activities (ribonuclease H, integrase and protease) that are essential for viral replication. HIV belongs to the lentivirus subfamily, members of which are characterized by several additional open reading frames (ORF) not found in simple retroviruses (FIG. 1). These ORFs all appear following gag-pol sequences, either immediately preceding the env sequences or overlapping it, and at least in one case, nef, extending well into the 3' Long Terminal Repeat (LTR). These ORFs code for non-structural viral proteins readily detectable in the cells. Much evidence has accumulated indicating that these gene products, collectively referred to as auxiliary proteins , are capable of modulating viral replication and infectivity.

HIV-1 possesses at least six such auxiliary proteins, namely, Vif, Vpr, Tat, Rev, Vpu and Nef. The closely related HIV-2 does not code for Vpu, but codes for another unrelated protein, Vpx, not found in HIV-1. Mutations affecting either Tat or Rev severely impair viral replication indicating that these two auxiliary proteins are essential for viral replication. However, at least in vitro, mutations affecting other auxiliary proteins result in minimal effect on the viral replication kinetics. Hence, these proteins have been dubbed dispensable or non-essential for in vitro replication, and are usually referred to as accessory gene products.

In the past few years, it has become evident that while these "accessory" genes are not required for productive replication, they are nonetheless capable of affecting replication events, even in vitro. More importantly, recent data indicates that they may affect pathogenesis in vivo.

The vpr gene encodes a 14 kDa protein (96 amino acids) in most strains of HIV-1 (FIG. 2; Myers et al., 1993, *Human Retroviruses and AIDS* 1993 I–II, Los Alamos National Laboratory, New Mexico, USA), although the open reading frame is often truncated in viral strains extensively passaged in tissue culture. The vpr open reading frame is also present in HIV-2 isolates and in most but not in all HIV isolates. A sequence similar to HIV-1 vpr is also found in Visna virus. Recent amino acid comparison between HIV-2 vpr and vpx showed regions of similarity suggesting that vpx in the HIV-2/SIV group may have arisen by duplication of the vpr gene (FIG. 2; Myers et al., 1993, Human Retroviruses and AIDS 1993 I–II, Los Alamos National Laboratory, New Mexico, USA). The Vpr protein is made from a singly spliced rev-dependent mRNA species that accumulates late in infection. The Vpr protein of HIV and SIV have recently been shown to be present in mature viral particles in multiple copies. Interestingly, Vpr and Vpx are the first regulatory protein of any retrovirus found to be associated with viral particles. Other regulatory proteins, such as tat, Rev, Nef, Vif and Vpu are not virion-associated. The assembly and maturation of HIV-1 viral particles is a complex process in which the structural Gag, Pol and Env gene products are expressed in the form of polyprotein precursors. The Gag proteins of HIV play a central role in virion assembly and budding. Gag proteins are initially synthesized as myristylated polyprotein precursors, $Pr55^{gag}$ and $Pr160^{gag\text{-}pol}$, which are transported to the inner face of the plasma membrane where they can direct particle formation, even in the absence of other viral proteins. Complete budding leads to formation of immature particles, followed by HIV protease mediated cleavage of the Gag and Gag-Pol precursor polyproteins and formation of mature HIV particles with condensed core. The mature virion proteins derived from cleavage of the gag-encoded precursor, $Pr55^{gag}$, include the p17 matrix protein (MA), the p24 capsid protein (CA), the p7 nucleocapsid protein (NC), and a small proline-rich peptide of approximately 6 kDa designated p6 which are linked in this order in the polyprotein precursor. Vpr is not part of the virus polyprotein precursors and its incorporation occurs by way of an interaction with a component normally found in the viral particle. It was recently reported that the HIV-1 Vpr could be incorporated in trans into viral-like particle (VLP) originating from expression of the $Pr55^{gag}$ only (Lavallée et al., 1994, J. Virol., 1926–1934). Data from this and other studies indicate that Vpr incorporation appeared to result from a direct interaction of Vpr with the carboxy-terminal region of the $Pr55^{gag}$ polyprotein (Paxton et al. 1993, Journal of Virology, 67(12):7229–7237; Lu et al., 1993, Journal of Virology, 67(1):6542–6550).

Functional studies indicated that the full length vpr protein could confer favorable growth properties to viruses. The increase in virion production is more pronounced in primary macrophages in both HIV-1 and HIV-2 systems, suggesting that Vpr function may be important in specific target cells. Interestingly, while mutations affecting HIV-1 vpr do not affect replication in peripheral blood mononuclear cells (PBMC), mutations in HIV-2 vpr results in a measurable impairment in these cells. Similarly, a recent study using anti-sense RNA directed against vpr inhibited viral replication in primary macrophages but not in transformed T-cells. Previous work indicated that this rapid growth advantage may be conferred by the weak transactivation property of Vpr on HIV-LTR directed gene expression (European Patent Application published under No. 474,797 on Mar. 18, 1992 in the name of DANA FARBER CANCER INSTITUTE). Cotransfection experiments suggest that vpr could augment the expression of a reporter gene from several heterologous promoters by approximately three to ten fold.

The carboxyl terminal sequence of Vpr have been shown to be important for Vpr mediated transactivation as prematurely truncated proteins are non-functional and are not packaged into the virion. Interestingly, a recent report also indicated that the carboxyl terminal of the protein is important for nuclear localization (Lu et al., 1993, Journal of Virology, 67(1):6542–6550). A specific vpr responsive LTR sequence was not identified and the exact mechanism by which vpr augments reporter gene expression is not clear. The precise mode of action of vpr is yet to be established. However, the presence of vpr in the viral particle suggests that this protein has a role in the early stage of infection. Virion-associated non-structural proteins in many viral systems play a pivotal enzymatic functions in early replication steps, either because cellular homologues are unavailable or are sequestered, for example, in the nucleus. It is possible that Vpr is one such protein, capable of modulating early viral specific functions such as reverse transcription stabilization of early RNA or DNA intermediates, transport to the nucleus or integration. It is equally possible that Vpr could function at an early step, in a non-viral specific manner, by triggering processes that could make the cellular environment congenial to establish viral infection. In this regard, HIV-1 Vpr has been reported to be involved in inducing cellular differentiation in rhabdomyosarcoma cells (Levy et al., 1993, Cell, 72:541–550). Finally, because Vpr is synthesized late in the infection cycle of HIV, it may regulate the morphogenesis of the virus (late events) by an unknown mechanism or constitute a structural protein involved in the integrity of the virions.

The use of transport polypeptides for biological targeting is well known and was adapted to many fields. The HIV Tat protein has been described to effect the delivery of molecules into the cytoplasm and nuclei of calls (international Application published on Mar. 3, 1994 as No. WO 94/04686 in the name of BIOGEN, INC.). However, the Tat transport polypeptides can not allow the delivery of molecules to HIV virions. Viral proteins such as Gag of Rous sarcoma virus and Moloney murine leukemia virus and portion of HIV-1 Gag protein have been used as carrier for incorporation of foreign antigens and enzymatic markers into retroviral particles (Wagner et al., 1994, Virology, 200:162–175). However, most of the Gag protein sequences are essential for efficient viral particles assembly, thus limiting the use of such virion components as carrier.

It would be highly desirable to be provided with means to target molecules to mature HIV-1 and HIV-2 virions to affect their structural organization and/or functional integrity.

It would also be highly desirable to be provided with a Vpr protein, a Vpx protein or fragments thereof which permit the development of chimeric molecules that can be specifically targeted into the mature HIV-1 and HIV-2 virions to affect their structural organization and/or functional integrity, thereby resulting in treatment of HIV-1 and HIV-2 infections.

It would also be highly desirable to be provided with a therapeutic agent which permit the targeting of chimeric molecules into the mature HIV-1 and HIV-2 virions as a treatment for HIV-1 and HIV-2 infections.

It would also be highly desirable to be provided with the identification of the protein interaction responsible for Vpr or Vpx incorporation in the mature HIV-1 and HIV-2 virions.

It would also be highly desirable to be provided with means to target the protein interaction responsible for Vpr or Vpx incorporation in the mature HIV-1 and HIV-2 virions to affect their functional integrity.

It would also be highly desirable to be provided with a Vpr protein fragment, a Vpx protein fragment, a p6 protein or p6 protein fragment which permits the development of molecules that can specifically interfere with the protein interaction responsible for Vpr or Vpx incorporation in the mature HIV-1 and HIV-2 virions to affect their functional integrity, thereby resulting in treatment of HIV-1 and HIV-2 infections.

It would also be highly desirable to be provided with a therapeutic agent which interferes with the protein interaction responsible for Vpr or Vpx incorporation in the mature HIV-1 and HIV-2 virions as a treatment for HIV-1 and HIV-2 infections.

SUMMARY OF THE INVENTION

One aim of the present invention is to provide with means to target molecules to mature HIV-1 and HIV-2 virions to affect their structural organization and/or functional integrity.

Another aim of the present invention is to provide a Vpr protein, a Vpx protein or fragments thereof which permit the development of chimeric molecules that can be specifically targeted into the mature HIV-1 and HIV-2 virions to affect their structural organization and/or functional integrity, thereby resulting in treatment of HIV-1 and HIV-2 infections.

Another aim of the present invention is to provide a therapeutic agent which permit the targeting of chimeric molecules into the mature HIV-1 and HIV-2 virions as a treatment for HIV-1 and HIV-2 infections.

Another aim of the present invention is to provide the identification of the protein interaction responsible for Vpr or Vpx incorporation in the mature HIV1 and HIV-2 virions.

Another aim of the present invention is to provide means to target the protein interaction responsible for Vpr or Vpx incorporation in the mature HIV-1 and HIV-2 virions to affect their functional integrity.

Another aim of the present invention is to provide a Vpr protein fragment, a Vpx protein fragment, a p6 protein or p6 protein fragment which permits the development of molecules that can specifically interfere with the protein interaction responsible for Vpr or Vpx incorporation in the mature HIV-1 and HIV-2 virions to affect their functional integrity, thereby resulting in treatment of HIV-1 and HIV-2 infections.

Another aim of the present invention is to provide a therapeutic agent which interferes with the protein interaction responsible for Vpr or Vpx incorporation in the mature HIV-1 and HIV-2 virions as a treatment for HIV-1 and HIV-2 infections.

In accordance with the present invention there is provided a protein for targeting into a mature HIV-1 or HIV-2 virion, which comprises a sufficient number of amino acids of a Vpr protein, a Vpx protein, functional derivatives or fragments thereof, wherein the protein interacts with a Gag-precursor protein of the mature virion and is incorporated by the virion. More specifically, the protein interacts with the protein p6 which is a component of the Gag-precursor protein.

More specifically, the protein of the present invention, further comprises a protein fragment covalently attached to its N- or C-terminal to form a chimera protein which is also incorporated by the mature virion. Such an attached protein fragment of the present invention consists of amino acid sequences having RNase, protease activities or amino acid sequences capable of creating steric hindrance during virion morphogenesis.

More specifically, the protein of the present invention, further comprises a molecule to form a protein-molecule complex which is also incorporated by the mature virion. Such a molecule is selected from the group consisting of anti-viral agents, RNase, proteases, and amino acid sequences capable of creating steric hindrance during virion morphogenesis. The molecule of the protein-molecule complex of the present invention affects the structural organization or functional integrity of the mature virion by steric hindrance or enzymatic disturbance of the virion.

In accordance with the present invention there is also, provided a protein which interferes with Vpr or Vpx incorporation into HIV-1 and HIV-2 virions and which comprises a sufficient number of amino acids of a Vpr protein fragment, a Vpx protein fragment, a p6 protein, p6 protein fragment, or its functional derivative thereof, wherein the protein interacts either with Gag-precursor or with Vpr or Vpx protein to compete with the Vpr-Gag-precursor or Vpx-Gag-precursor interaction and consequently to interfere with the incorporation of the native Vpr into the virions and to substantially prevent replication of the mature virion.

In accordance with the present invention there is also provided a method of substantially reducing HIV expression or replication in a patient infected with HIV-1 or HIV-2, which comprises administering at least one therapeutic agent selected from the group consisting of the protein or DNA sequences encoding the protein of the present invention, to the patient in association with a pharmaceutically acceptable carrier. The administration step of the method is effected intracellularly for anti-viral treatment including gene therapy or immunization as the patient or by DNA transfection of the patient's hematopoietic cells followed by readministration of the transfected cells.

Accordingly, in view of two different approaches of the present invention, therapeutic agents which may be used in accordance with the present invention are selected from the group consisting of a protein of the present invention including Vpr/Vpx chimera protein comprising RNase, proteases or amino acids sequences capable of creating steric hindrance during virion morphogenesis, Vpr/Vpx protein fragment, p6 protein and p6 protein fragment, and DNA sequences encoding a protein of the present invention.

In accordance with the present invention there is also provided a pharmaceutical composition for reducing HIV expression in a patient infected with HIV-1 or HIV-2, which comprises a sufficient amount of the therapeutic agent of the present invention in association with a pharmaceutically acceptable carrier.

BRIEF DESCRIPTION OF THE DRAWINGS

FIG. 2 shows the amino acid sequences of native Vpr protein from HIVLAI isolate and native Vpr and Vpx proteins from HIV2ROD isolate.

DETAILED DESCRIPTION OF THE INVENTION

Figure 1:
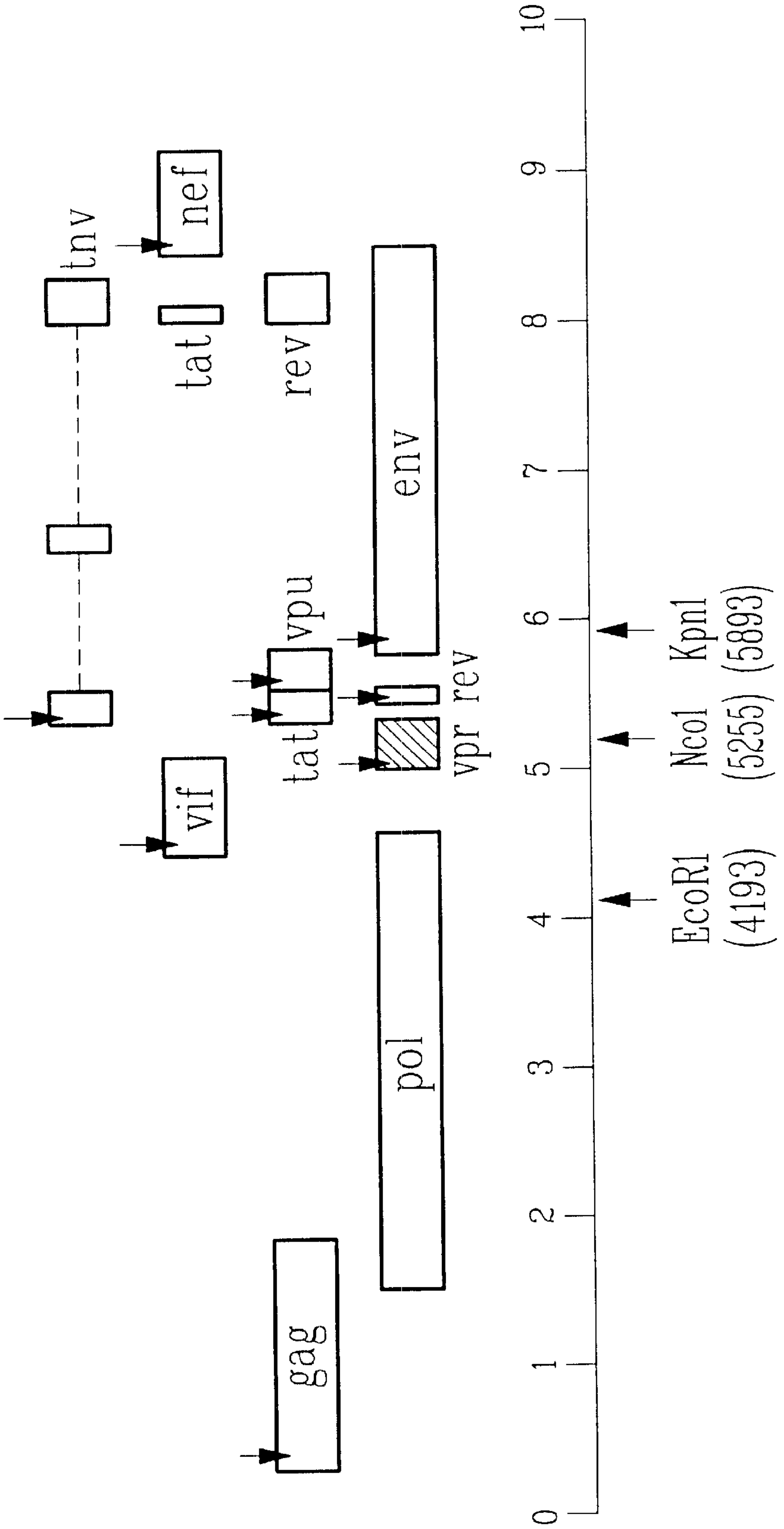
FIG. 1 shows the HIV genetic organization, here the vpr gene is positioned in the central region.

In accordance with the present invention, two different approaches using the Vpr/Vpx protein and p6 protein are described herein for the treatment of HIV-1 and HIV-2 infections.

In the first approach, the region of Vpr/vpx protein, which is involved in the protein interaction responsible for Vpr/Vpx virion-incorporation, is used as a carrier to target molecules to a mature HIV-1 and HIV-2 virions.

In the second approach, the region of Vpr/Vpx protein or alternatively the region of Gag-precursor, which are both involved in the protein interaction responsible for Vpr/Vpx virion-incorporation, is used to interfere with the native viral Vpr/Vpx protein incorporation.

In general, the abbreviations used herein for designating the amino acids are based on recommendations of the IUPAC-IUB Commission on Biochemical Nomenclature (Biochemistry, 1972, 11:1726–1732).

In accordance with the first approach of the present invention, there is provided the use of the Vpr or vpx protein, which is referred to as the "Vpr/Vpx" protein, functional derivatives or fragments thereof for the targeting of molecules to the HIV-1 and HIV-2 virions.

The preferred Vpr/Vpx protein, which is used in accordance with the first approach of the present invention, contains a sufficient number of amino acids corresponding to at least one of the following amino acid sequences consisting of:

```
Met Glu Gln Ala Pro Glu Asp Gln Gly Pro Gln Arg Glu Pro His Asn  (SEQ ID NO:1);
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe Arg Ile Gly Cys Arg His Ser Arg
65                  70                  75                  80

Ile Gly Val Thr Gln Gln Arg Arg Ala Arg Asn Gly Ala Ser Arg Ser
                85                  90                  95

Met Ala Glu Ala Pro Thr Glu Leu Pro Pro Val Asp Gly Thr Pro Leu  (SEQ ID NO:2); and
1               5                   10                  15

Arg Glu Pro Gly Asp Glu Trp Ile Ile Glu Ile Leu Arg Glu Ile Lys
            20                  25                  30

Glu Glu Ala Leu Lys His Phe Asp Pro Arg Leu Leu Ile Ala Leu Gly
        35                  40                  45

Lys Tyr Ile Tyr Thr Arg His Gly Asp Thr Leu Glu Gly Ala Arg Glu
    50                  55                  60

Leu Ile Lys Val Leu Gln Arg Ala Leu Phe Thr His Phe Arg Ala Gly
65                  70                  75                  80

Cys Gly His Ser Arg Ile Gly Gln Thr Arg Gly Gly Asn Pro Leu Ser
                85                  90                  95

Ala Ile Pro Thr Pro Arg Asn Met Gln
            100                 105

Met Thr Asp Pro Arg Glu Thr Val Pro Pro Gly Asn Ser Gly Glu Glu  (SEQ ID NO:3);
1               5                   10                  15

Thr Ile Gly Glu Ala Phe Ala Trp Leu Asn Arg Thr Val Glu Ala Ile
            20                  25                  30

Asn Arg Glu Ala Val Asn His Leu Pro Arg Glu Leu Ile Phe Gln Val
        35                  40                  45

Trp Gln Arg Ser Trp Arg Tyr Trp His Asp Glu Gln Gly Met Ser Glu
    50                  55                  60

Ser Tyr Thr Lys Tyr Arg Tyr Leu Cys Ile Ile Gln Lys Ala Val Tyr
65                  70                  75                  80

Met His Val Arg Lys Gly Cys Thr Cys Leu Gly Arg Gly His Gly Pro
                85                  90                  95

Gly Gly Trp Arg Pro Gly Pro Pro Pro Pro Pro Pro Pro Gly Leu Val
            100                 105                 110
PS
```

functional fragments or derivatives thereof, wherein the Vpr/Vpx protein, its fragments or derivatives thereof have retained the virion-incorporation function of the native Vpr/Vpx protein.

The expression "functional fragments or derivatives" when used herein is intended to mean any substitutions, deletions and/or additions of amino acids that do not affect the virion-incorporation function of the Vpr native protein.

In accordance with the first approach of the present invention, a preferred Vpr/Vpx chimera protein comprises an amino acid sequence of a Vpr/Vpx protein or a functional derivative thereof and a molecule attached to the amino acid sequence. Said molecule may be covalently attached at the N- or C-terminal of the amino acid sequence or it may be attached to the amino acid sequence at any amino acid position by chemical cross-linking or by genetic fusion.

A preferred molecule used in accordance with the present invention may be selected from the group consisting of an anti-viral agent and a second amino acid sequence which contains a sufficient number of amino acids corresponding to RNase, proteases, or any protein capable of creating steric hindrance during virion morphogenesis.

The Vpr/Vpx chimera protein in accordance with the first approach of the present invention may be used for the targeting of molecules into the mature virions of HIV-1 and HIV-2, such as polypeptides, proteins and anti-viral agents, among others.

In accordance with the second approach of the present invention, there is provided the use of Vpr/Vpx protein fragments, p6 protein, p6 protein fragment, or functional derivatives thereof which interfere with the native Vpr/Vpx incorporation into HIV-1 and HIV-2 virions. Again, the Vpr/Vpx protein fragments, p6 protein, p6 protein fragments, or functional derivatives thereof have retained their ability to interact with the native Vpr/Vpx or p6 protein, respectively. The expression "functional derivatives" when used herein is intended to mean any substitutions, deletions and/or additions of amino acids that do not affect the virion-incorporation function of the native Vpr/Vpx or p6 protein.

The preferred Vpr/Vpx protein fragments which is used in accordance with the second approach of the present invention is a fragment of the following amino acid sequence consisting of:

```
Met Glu Gln Ala Pro Glu Asp Gln Gly Pro Gln Arg Glu Pro His Asn  (SEQ ID NO:4)
1               5                   10                  15

Glu Trp Thr Leu Glu Leu Leu Glu Glu Leu Lys Asn Glu Ala Val Arg
            20                  25                  30

His Phe Pro Arg Ile Trp Leu His Gly Leu Gly Gln His Ile Tyr Glu
        35                  40                  45

Thr Tyr Gly Asp Thr Trp Ala Gly Val Glu Ala Ile Ile Arg Ile Leu
    50                  55                  60

Gln Gln Leu Leu Phe Ile His Phe
65                  70
```

wherein said fragment is a region of the Vpr/Vpx protein which binds to Gag-precursor.

The preferred p6 protein which is used in accordance with the second approach of the present invention contains a sufficient number of amino acids corresponding to the following amino acid sequences consisting of:

```
Leu Gln Arg Ser Pro Glu Pro Thr Ala Pro Pro Glu Glu Ser Phe Arg  (SEQ ID NO:5).
1               5                   10                  15

Ser Gly Val Glu Thr Thr Thr Pro Pro Gln Lys Gln Glu Pro Ile Asp
            20                  25                  30

Lys Glu Leu Tyr Pro Leu Thr Ser Leu Arg Ser Leu Phe Gly Asn Asp
        35                  40                  45

Pro Ser Ser Gln
    50
```

The Vpr/Vpx fragment, p6 protein and p6 protein fragment in accordance with the second approach of the present invention may be used for interfering with the virion-Incorporation of native Vpr/Vpx into HIV-1 and HIV-2 virions.

The purpose of the treatment in accordance with the first and second approaches of the present invention may be a prevention or a treatment. The product in these treatment procedures may be expressed intracellularly or provided to the cell via the blood stream.

In accordance with the first approach of the present invention, the expressed product may be This effective in the production of defective viral particles, for instance, viral particles with Vpr/Vpx chimera proteins such as the ones associated with virally directed protease or nuclease or with a portion of protein which affects the structural organization and/or functional integrity of the virions.

The treatment in accordance with the second approach of the present invention may consists in the production of viral particles having substantially reduced replication capacity, for instance, HIV-1 and HIV-2 viral particles devoided of functional level of Vpr/Vpx protein as a consequence of Vpr-Gag-precursor or Vpx-Gag-precursor interaction interference using Vpr/Vpx protein fragments, p6 protein and p6 protein fragments.

HIV-1 vpr Regions Associated with Viral Particles Incorporation

Figure 3:
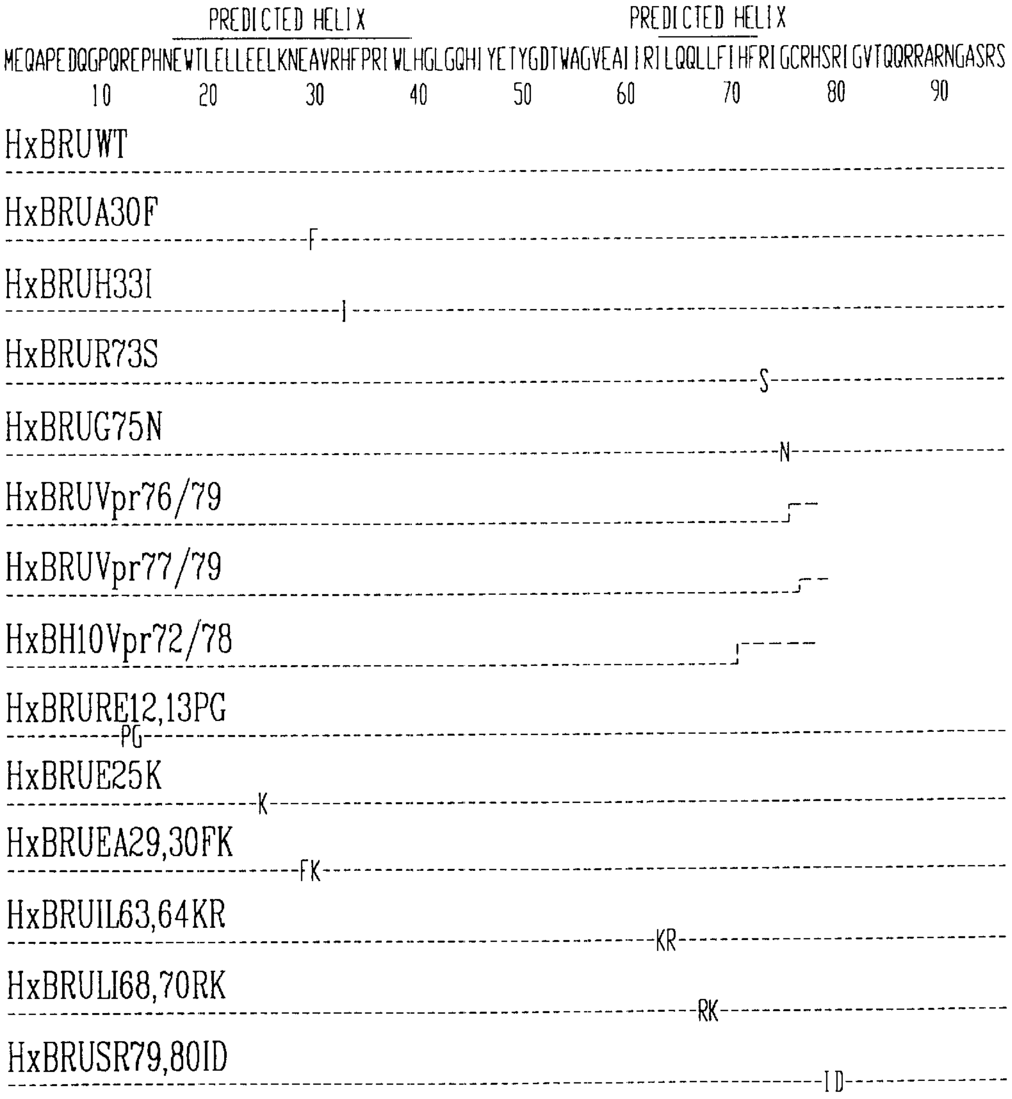
FIG. 3 shows the mutagenesis chart of the vpr gene of HxBH10 or pHxBRU template Of HIV-1.

The substitution mutations and deletions of vpr were generated by site-directed mutagenesis. Wildtype vpr sequence and location of predicted alpha-helix structures are indicated at the top of FIG. 3. Oligonucleotide-directed mutagenesis of the vpr gene was carried out on DNA fragments derived from pHxBRU template (FIG. 3) and then cloned into an infectious provirus (pHxBRU) (Lavallée et al., 1994, J. Virol., 68;1926–1934). Amino acid substitutions are indicated. BRUR 77/79, BRUR 76/79 and HxBH10 72/78 (Yao et al., 1992, Journal of Virology, 66(8):5119–5126) are truncated vpr proteins with additional unrelated amino acids generated by frame shift mutations.

Figure 4A:
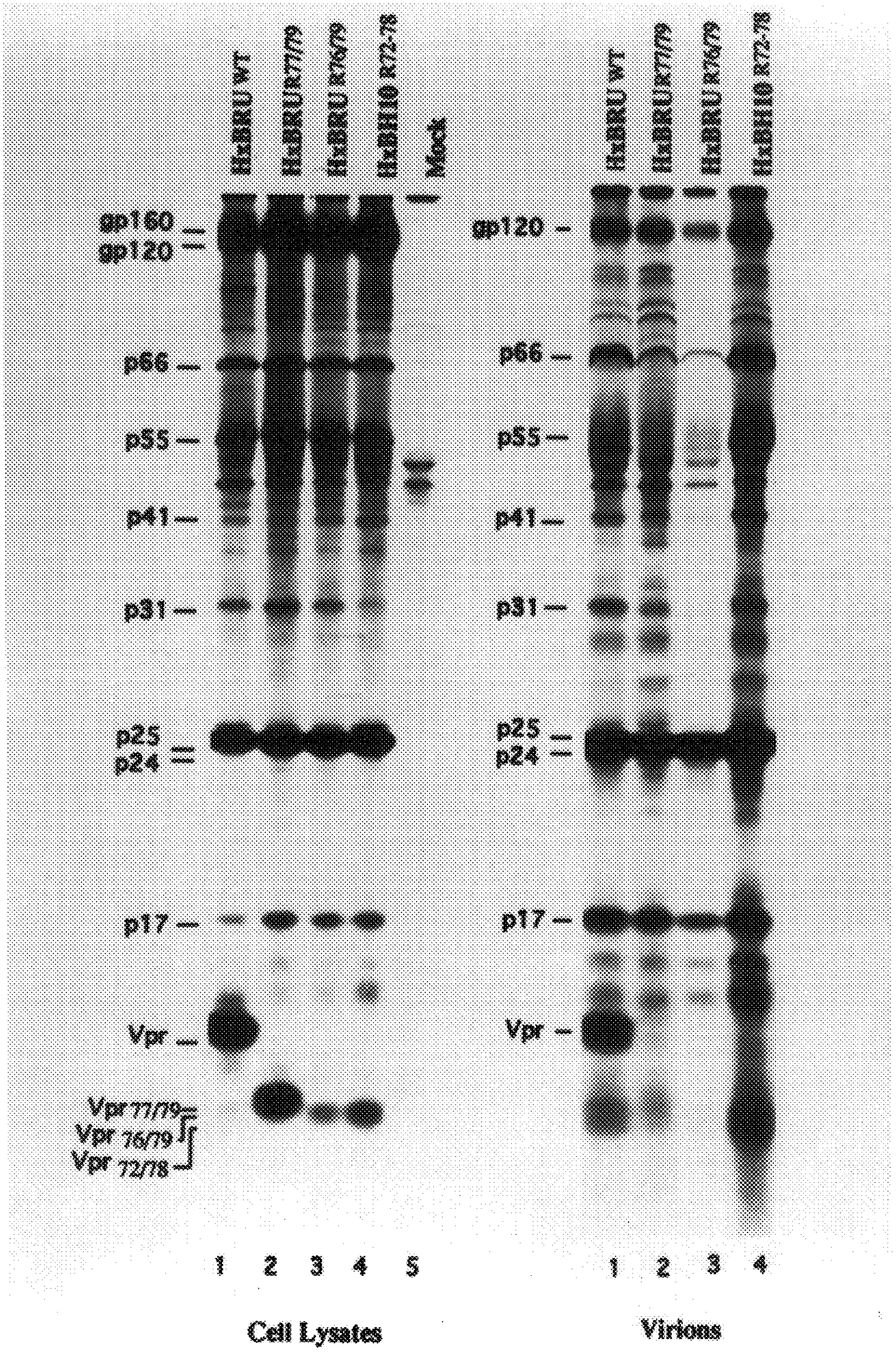
FIGS. 4A, 4B, and 4C show the analysis of Vpr present in lysates and supernatants of MT4 cells infected with HIV-1 containing various mutated or truncated vpr mutants.
Figure 4B:
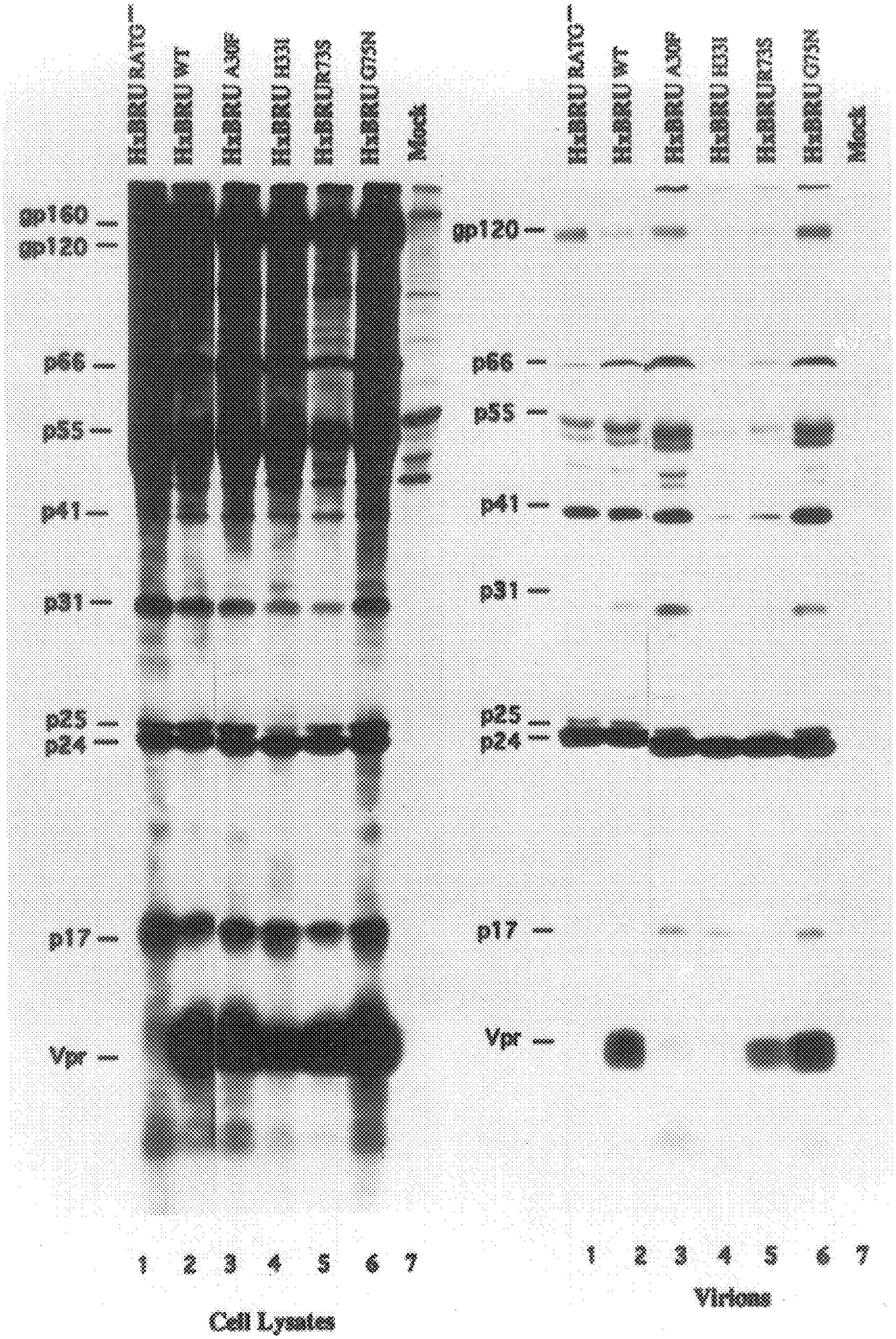
Figure 4C:
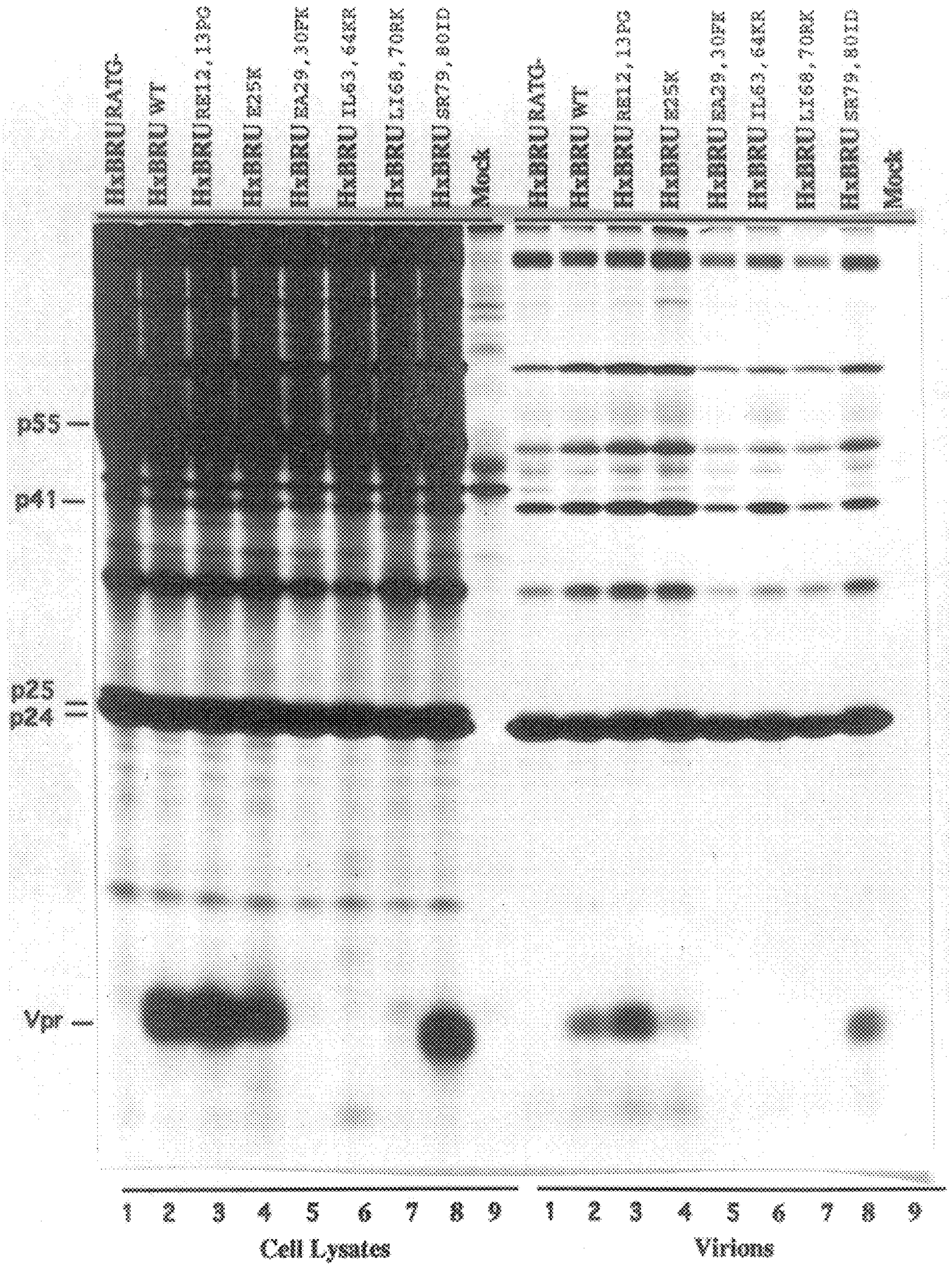

FIGS. 4A, 4B and 4C are autoradiograms that illustrate the analysis of truncated or substituted Vpr mutants in HIV-1 infected MT4 cells. $2 \times 10^6$ T-lymphoid cells (MT4) were infected (or transfected, FIG. 4C) with HIV-1 which contain wildtype or truncated Vpr (FIG. 3), as indicated at the top of the autoradiograms. The position of HIV-1 viral proteins are indicated at the left of the autoradiograms (Vpr). At 40 h post-transfection, cells were labelled with 100 $\mu$Ci of $^{35}$S-methionine and 100 $\mu$Ci of $^{3}$H-leucine for 16 h. Virions were pelleted from cell-free supernatants by ultracentrifugation at 35,000 rpm through, a 20% sucrose cushion for 2 h. Both cells (left panel) and sucrose cushion pelleted viruses (right panel, FIGS. 4A, 4B & 4C) were lyzed in RIPA buffer (140 mM NaCl, 8 mM $NaHPO_4$, 2 mM $NaH_2PO_4$, 1% Nonidet™ P-40, 0.5% sodium deoxycholate, 0.05% SDS) and immunoprecipitated with a HIV-1 positive human serum combined with a rabbit anti-Vpr Serum. Proteins were then analyzed on a sodium dodecyl sulfate (SDS) 12.5%–17% gradient polyacrylamide gel electrophoresis (PAGE) and autoradiography. Quantification of virion associated vpr and protein stability was determined by densitometric scanning of the autoradiograms using a laser densitometer (Molecular Dynamics™ densitometer).

Figure 5B:
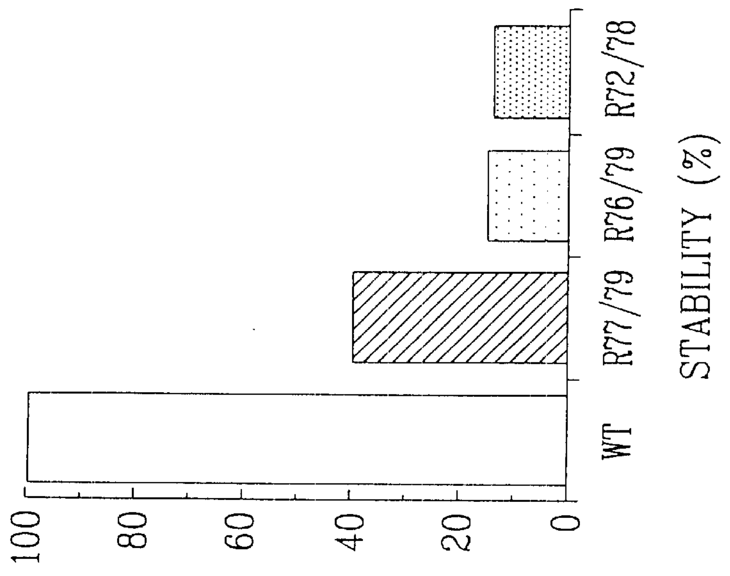
FIG. 5 shows the stability of the truncated or mutated Vpr protein in infected MT4 cells.
Figure 5A:
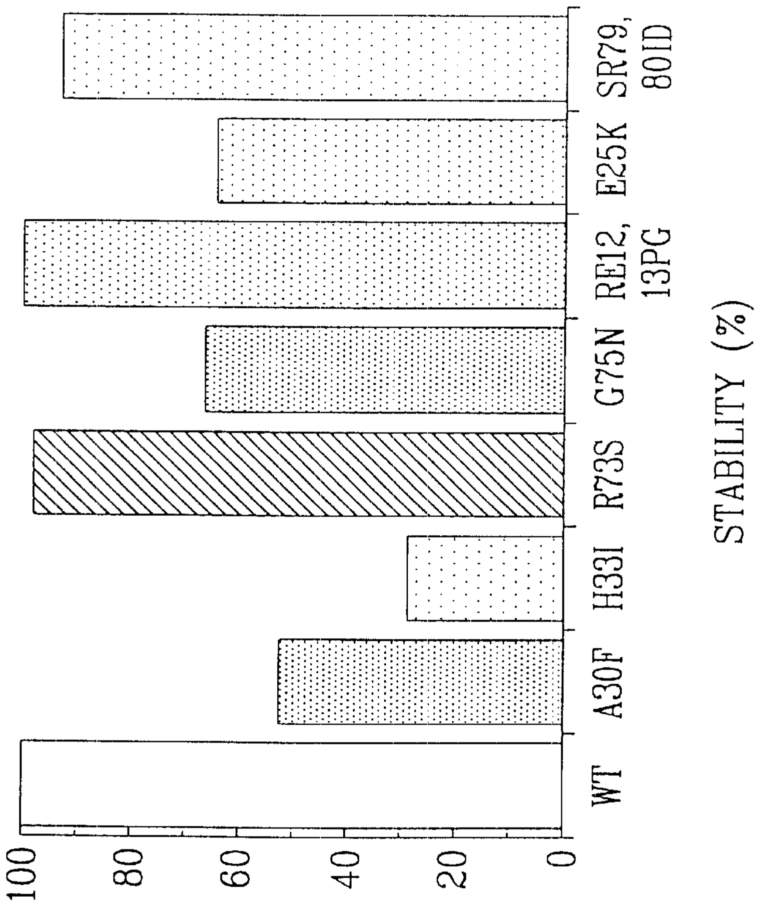

FIG. 5 shows the stability of different truncated (FIG. 5B) or substituted (FIG. 5A) Vpr mutants in HIV-1 infected cell lysates. The intensity of wildtype or mutated Vpr proteins were quantified relative to the intensity of the p66 reverse transcriptase (RT) bands. Immunoprecipitation analysis has shown that all truncated Vpr proteins were present at low level in cell lysates suggesting the importance of the C-terminal region for Vpr stability (FIGS. 4A and 5B).

Figure 6:
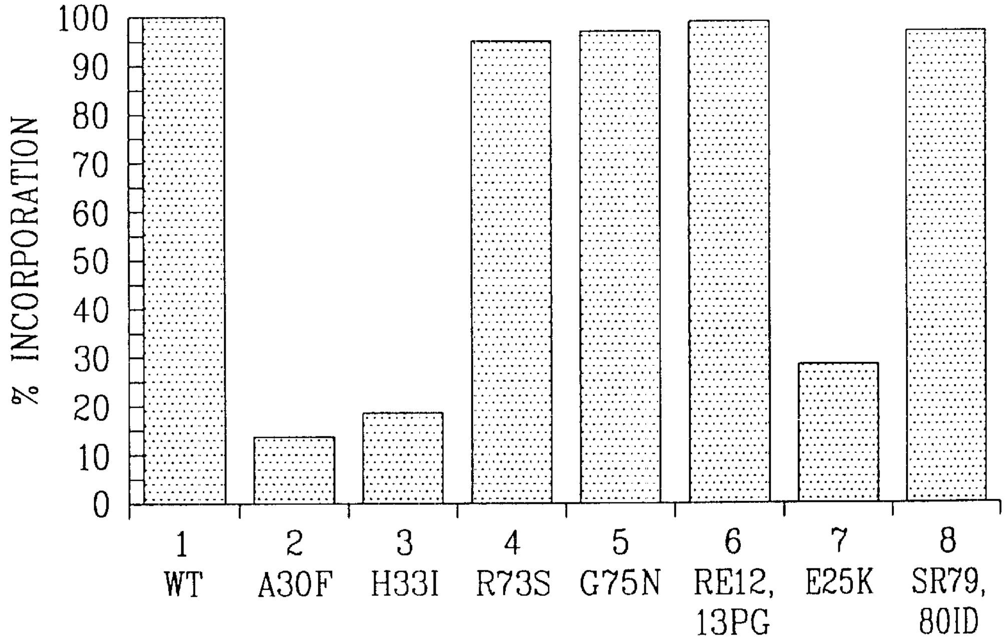
FIG. 6 shows quantification of the incorporation of different mutated Vpr into HIV-1 virions.

FIG. 6 shows the efficiency of incorporation of different mutated Vpr into HIV-1 virions. The incorporation of mutated Vpr into virions was also evaluated by densitometric analysis. The intensity of Vpr proteins into virions were quantified relative to at the intensity of the p6g reverse transcriptase (RT) bands in autoradiograms presented in FIGS. 4B and 4C. The results of the present invention demonstrate that substitution mutations (A30F, H331 and E25K) in the N-terminal portion of vpr significantly impair the incorporation of vpr protein into virions (FIGS. 4B, 4C and 6). Interestingly, this region of the protein is predicted to form an alpha helix conformation which is reminiscent of a structure involved in protein-protein interaction. These data indicate that the N-terminus of Vpr is important for vpr incorporation in the virion. This region will be further defined by analyzing additional vpr mutants f or their stability and virion-incorporation capacity.

HIV-1 GAG P6 Regions Associated with Vpr Incorporation

Figure 7A:
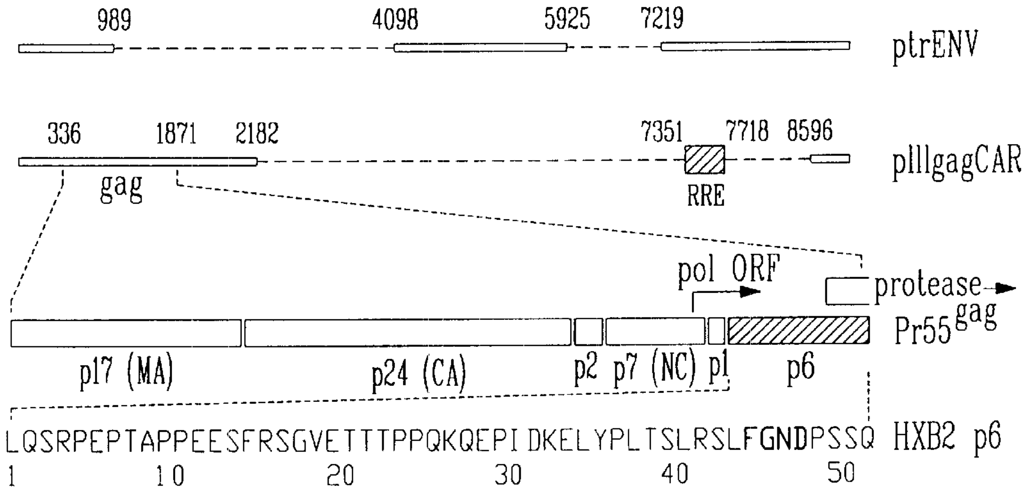
FIGS. 7A and 7B show the expression plasmids and the p6 construct plasmid expressing p6 mutant.
Figure 7B:
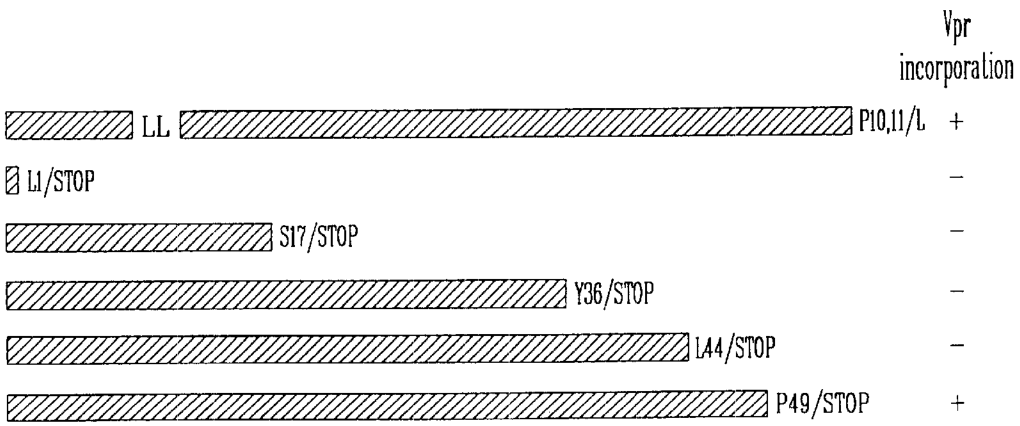

To investigate the mechanism of incorporation of Vpr, the ability of Gag-expressor plasmids, harboring deletions or mutations in the C-terminus of the capsid precursor, to target Vpr into virions in transiently transfected cells was tested. In this system two expresser plasmids described in FIG. 7A were cotransfected into COS-7 cells (Lavallée et al., 1994, J. Virol., 68:1926–1934; FIG. 7A). Deletions are shown as dotted lines between the thick lines. ptrENV contains 3109 (nucleotides 989 to 4098) and 1294 (nucleotides 5925 to 7219) base pair deletions affecting respectively gag, pol and the gp120 domain of env genes. ptrENV encodes Vpr at well as all HIV-1 auxilliary proteins (Vif, Tat, Rev, Vpu Nef and gp41). The pIIIgagCAR plasmid, a rev-dependent Gag expressor, which encodes $Pr55^{gag}$ and the protease domain of the pol gene (PR), contains the Rev-responsive element (RRE/CAR) sequence. P6 is the C-terminal components of the $Pr55^{gag}$ precursor (FIG. 7A). FIG. 7B illustrates the P6 constructs. Plasmids expressing P6 mutant were generated by introducing a termination codon or a substitution by polymerase chain reaction (PCR)-based site-directed mutagenesis in pIIIgagCAR plasmid.

Figure 8A:
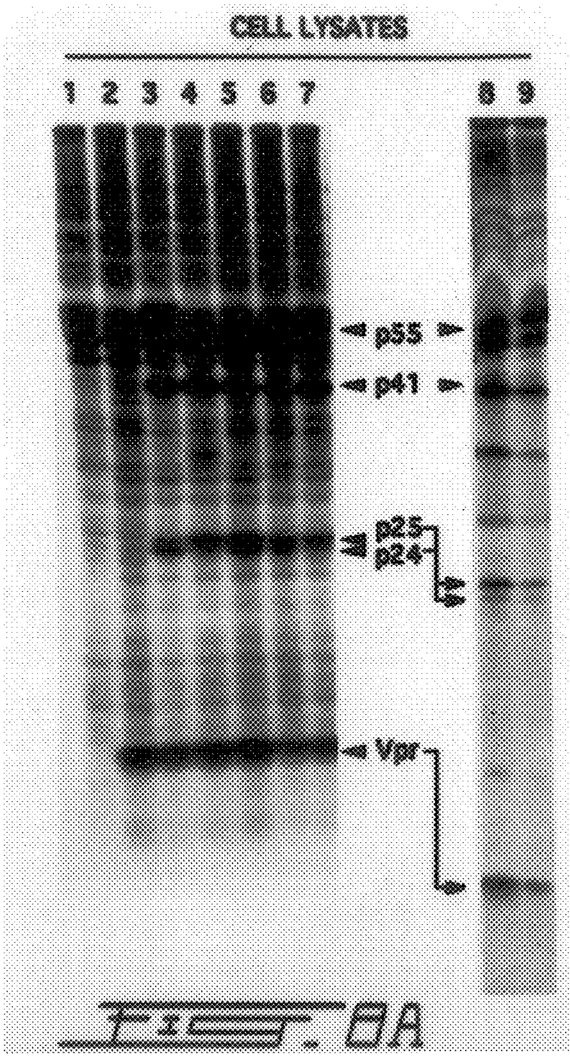
FIG. 8 shows the incorporation of Vpr into virions in the presence of different truncated or mutated Gag p6 protein.
Figure 8B:
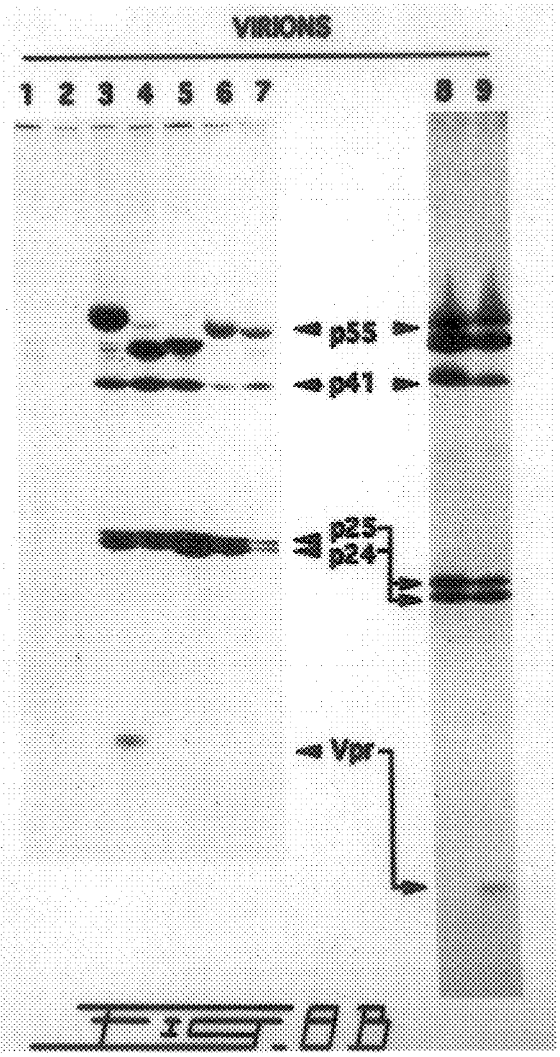

FIG. 8 illustrates the trans incorporation of Vpr into virus-like particles COS-7 cells were transfected with pIIIgagCAR plasmid (lane 1), or ptrENV plasmid (lane 2) or cotransfected with both constructs (lane 3). ptrENV was cotransfected with pIIIgagCAR based construct harboring a substitution or a premature termination codon in the p6 protein: L1/stop (lane 4), S17/stop (lane 5), Y36/stop (lane 6), P10,11L (lane 7), L44/stop (lane 8), P49/stop (lane 9). 48 h posttransfection [$^{35}$S]methionine- and [$^{3}$H]leucine-labelled viral proteins were immunoprecipitated, from the cell lysates or the cell-free supernatant centrifuged through a 20% sucrose cushion, with the HIV-1 positive human serum 162 mixed with a rabbit anti-Vpr polyclonal antibodies and analysed by SDS-PAGE and autoradiography.

The 14 kDa vpr product can be detected in the pelleted virions produced by cells cotransfected with pIIIgagCAR and ptrENV or the P49/stop or P10,11L mutants (FIG. 8, right panel, lanes 3, 9 and 7, respectively). However, virions produced from cells cotransfected in the presence of ptrENV and L1/stop, S17/stop, Y36/stop or L44/stop constructs lacked detectable Vpr (lanes 4, 5, 6 and 8, respectively). These results indicate a direct correlation between the absence of p6 and the loss of Vpr incorporation, suggesting that p6 is directly implicated. Moreover, deletion analysis suggests that the carboxyl terminal of p6 is important for Vpr incorporation. Indeed, a very short region corresponding to amino acid 45 to 48 inclusively (FGND) is critical for Vpr incorporation.

The present invention will be more readily understood by referring to the following examples which are given to illustrate the invention rather than to limit its scope.

EXAMPLE I

Incorporation in Trans of a Specific Epitope into Retroviral Particles

Figure 9:
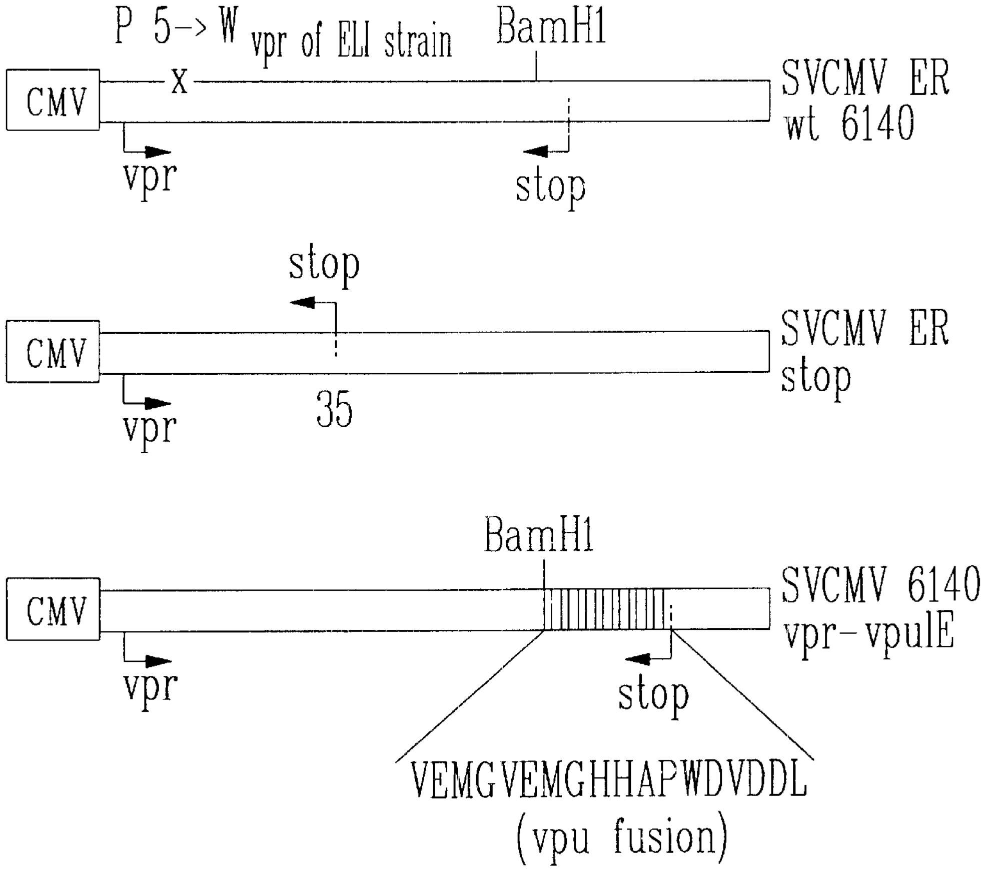
FIG. 9 shows the construction of a vector expressing a chimera protein between Vpr from HIV-1 Eli strain and a portion of the HIV-1 Vpu protein.

The ability of foreign antigen to be incorporated in trans into viral particles when fused to Vpr protein was examined. A vector which expresses a fusion protein containing the first 93 amino acids of Vpr from the Eli strain and a Vpu epitope was constructed (FIG. 9). The last 18 C-terminal amino acids of Vpu which contain a specific epitope (Cohen et al., 1988, Nature, 334:532–534) has been cloned at the BamHI restriction site located at the 3' end of the Vpr sequence. The chimera protein is Under the control of the cytomegalovirus (CMV) promoter (Lavallée et al., 1994, J. Virol., 68:1926–1934).

Figure 10:
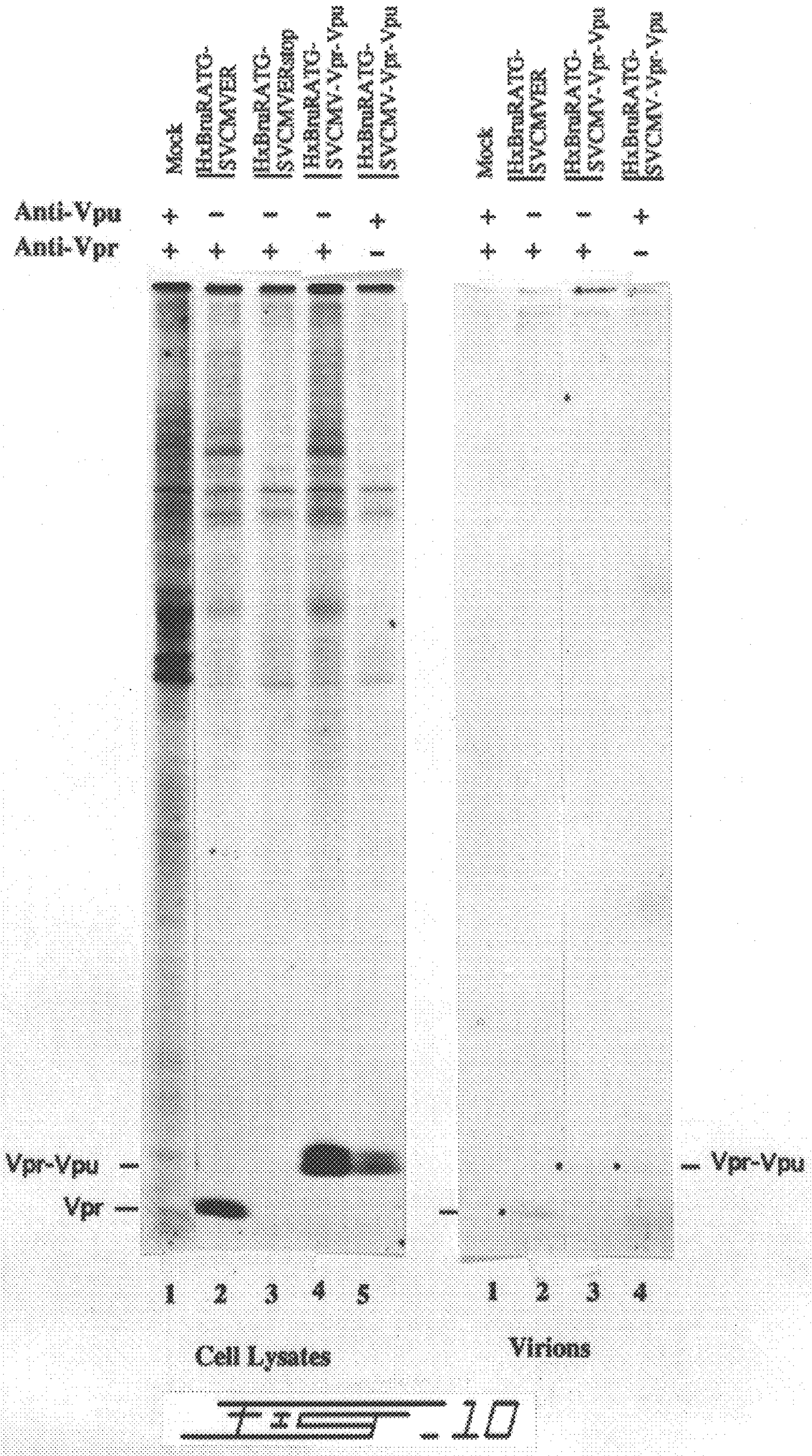
FIG. 10 shows the analysis of Vpr-Vpu chimera present in lysates and pelleted viral particles from COS cells co-transfected with the Vpr-Vpu expressor of FIG. 9 and a HIV-1 vpr-minus infectious molecular clone.

FIG. 10 shows the incorporation of Vpr-Vpu chimera into HIV-1 virions. One million COS-7 cells were cotransfected with the SVCMV-Vpr-Vpu chimera expressor and with a HIV-1 Vpr minus infectious molecular clone (pHxBRU-RATG$^-$). This HIV-1 clone was generated by introducing a GTG codon instead of the ATG initiation codon in the Vpr gene from the pHxBRU proviral clone (Lavallée et al., 1994, J. Virol, 68:1926–1934). 48 h post-transfection, cells were labelled with 200 $\mu$Ci of $^{35}$S-methionine and 200 $\mu$Ci of $^{3}$H-leucine for 16 h. Virions were pelleted from the cell-free supernatants by ultracentrifugation at 35,000 rpm through a 20% sucrose cushion for 2 h. Both cells (left panel) and sucrose cushion pelleted viruses (right panel) were lyzed in RIPA buffer (140 mM NaCl, 8 mM $NaHPO_4$, 2 mM $NaH_2PO_4$, 1% Nonidet™ P-40, 0.5% sodium deoxycholate, 0.05% SDS) and immunoprecipitated with a HIV-1 positive human serum combined with a rabbit anti-Vpr serum or with a rabbit anti-Vpu serum as indicated at the top of each lane of FIG. 10. The position of HIV-1 viral proteins are indicated at the left of the gel. Analysis of vpr products in the cell lysates and supernatants has revealed that 1) Vpr-Vpu chimera is stably expressed in transfected cells and 2) both Vpu ($\alpha$Vpu) and Vpr ($\alpha$Vpr) antisera are able to immunoprecipitate the chimera product from the virions (FIG. 10). These data indicate that the Vpu epitope was successfully transferred into virions when expressed in trans as a Vpr fusion product.

EXAMPLE II

Figure 11:
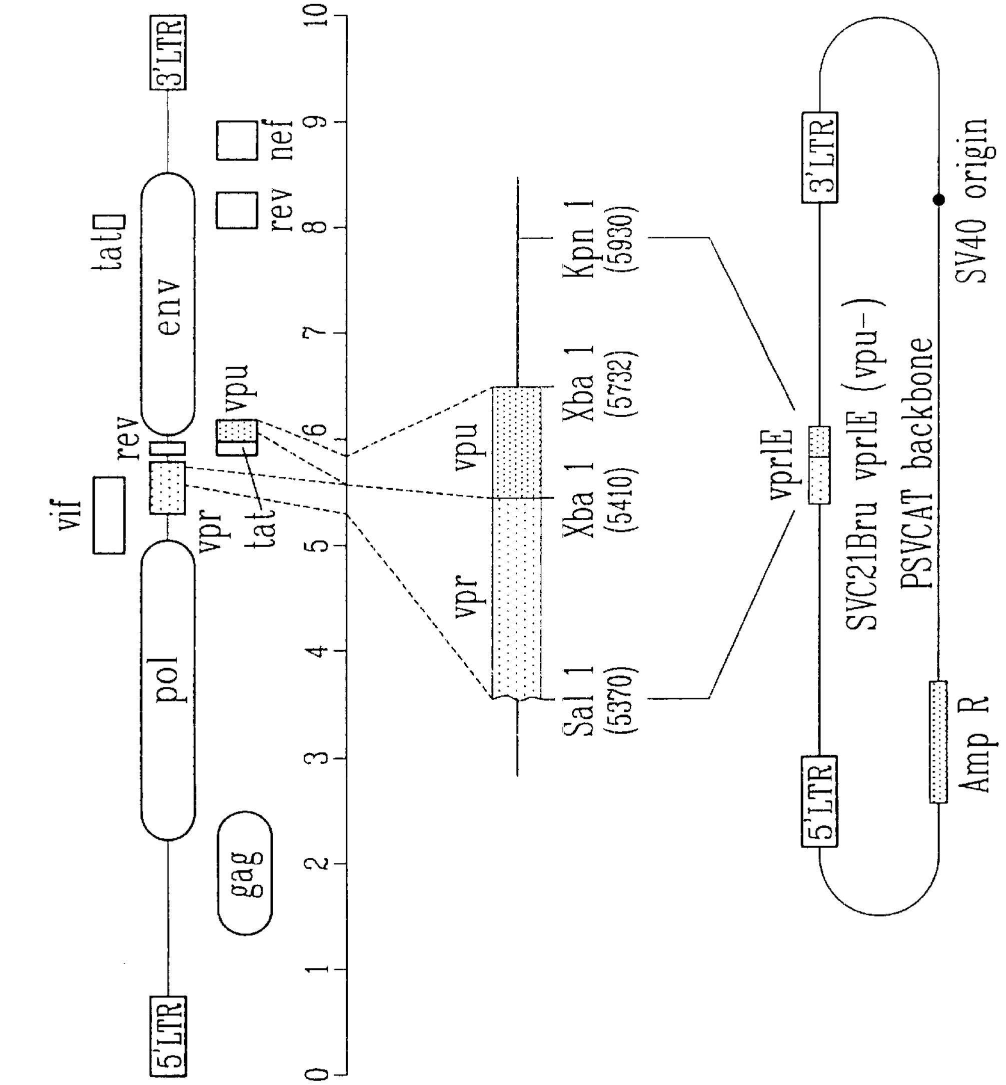
FIG. 11 shows the construction of a chimera protein between Vpr and a portion of the HIV-1 Vpu in the HIV-1 SVC21 BRU strain.

Incorporation of a Specific Epitope into Retroviral Particles From a HIV-1 Cloned Provirus Trans-incorporation of Vpr chimera protein into Vpr-virion in MT4 cells presents limitations due to the low transfection efficiency-obtained when two expression vectors are transfected in T cell lines. To address this question, a Vpr-Vpu fusion protein was cloned into a Vpu-minus HIV1 provirus plasmid. FIG. 11 shows a schematic representation of the proviral form of the retrovirus construct pHxBRU vprIE which encodes the Vpr sequence from pHxBRU (Lavallée et al., 1994, J. Virol., 68:1926–1934) fused to an immunodominant epitope tag corresponding to the last 18 amino acids of the BH10 Vpu-protein. This Vpu epitope is recognized by the specific Rabbit anti-Vpu peptide serum described by (Cohen et al., 1988, Nature, 334:532–534). This construction will be transfected in MT4 cells and the incorporation of the Vpr-Vpu fusion protein into virions will be measured. The introduction of a unique xbaI site at position 5410 in this construction without Vpu sequence. Vpr (pHxBRU RX) has also been designed to provide a unique cloning site in which any foreign DNA sequence could easily be covalently attached to the C-terminal end of Vpr.

The targeting of different Vpr fusion proteins in proviruses and their effects on viral replication and infectivity will further be tested in MT4 and Jurkat cell lines.

EXAMPLE III

Construction of Vpr Chimeric Molecules

Chimeric molecules are developed by fusion of Vpr sequences with either sequences encoding different enzymatic activities or random amino acid sequences of different lengths. To demonstrate that large molecules and functional enzymatic activities can be efficiently transferred into virions, Vpr is fused to prokaryotic genes such as β-galactosidase, luciferase or chloramphenicol acetyltransferase to generate Vpr chimeras. Rapid, sensitive and reproducible assays have been extensively described to measure the activity of these enzymes. COS cells are co-transfected with different chimera expressors and with Vpr-minus proviruses. Incorporation and enzymatic activities of fusion proteins associated to the viral particles is measured.

Vpr covalently attached to nuclease, protease or to peptide sequence of various length (vpr-steric hindrance peptide) are also constructed and the effect of these fusion proteins on the replication and infectivity of HIV in T cells are determined. Vpr chimera proteins are tested in two different systems to measure the effect of cis and trans expression; 1) the chimera proteins are cloned into the pHxBRU RX construction (described in Example II) and are transfected into MT4 CD4+ cells (cis expression); and 2) the chimera proteins cloned into expressors are co-transfected with a Vpr-minus provirus into COS cells (trans expression). In both cases, viral production is monitored. Degradation of viral RNA or proteins in the viral particles will lead to the production of defective virions. Incorporation of Vpr chimera which affect the structure and/or the organization of the HIV virion will affect its infectious properties.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for targeting a chimeric protein into a virion comprising expressing said chimeric protein in trans with respect to the genome of said virion, said chimeric protein comprising a first and second portion, wherein said first portion has a Vpr/Vpx virion incorporation domain which includes the predicted N-terminal alpha helix of the viral protein selected from the group consisting of HIV-1 Vpr, HIV-2 Vpr, HIV-2 Vpx, SIV Vpr and SIV Vpx and said second portion is fused to the C-terminal portion of said first portion; and wherein said virion contains the p6 domain of a Pr55gag precursor protein;

wherein the interaction of said Vpr/Vpx virion incorporation domain of said chimeric protein with said p6 domain of Pr55gag of the virion enables the targeting of said chimeric protein into said virion.

2. The method of claim 1 wherein said virion is an HIV-1 or HIV-2 virion.

3. A method for incorporating a chimeric protein into a viral particle when expressed in trans with respect to the genome thereof, comprising interacting said chimeric protein in a viral particle packaging cell line, with the p6 domain of a Pr55gag precursor protein present in said viral particle packaging cell line; said chimeric protein having a first and second portion, said first portion having a Vpr/Vpx virion incorporation domain which includes the predicted N-terminal alpha helix of a viral protein selected from the group consisting of HIV-1 Vpr, HIV-2 Vpr, HIV-2 Vpx, SIV Vpr and SIV Vpx; and said second portion is fused to the C-terminal portion of said first portion;

wherein the interaction of said Vpr/Vpx virion incorporation domain of said chimeric protein with said p6 domain of Pr55gag in said viral particle, enables the incorporation of said chimeric protein into said viral particle.

4. The method of claim 3 wherein said viral particle is a retroviral particle.

5. The method of claim 3 wherein said packaging cell line also harbors a retroviral vector.

6. The method of claim 4, wherein said retroviral particle is a HIV-1 or HIV-2 virion.

7. A method for incorporating a recombinant protein into a viral particle when expressed in trans with respect to the genome thereof, comprising interacting said recombinant protein in a viral particle packaging cell line with the p6 domain of a Pr55gag precursor protein present in said viral particle packaging cell line, wherein said recombinant protein comprises a Vpr/Vpx virion incorporation domain which includes the predicted N-terminal alpha helix of a viral protein sequence selected from the group consisting of HIV-1 Vpr, HIV-2 Vpr, HIV-2 Vpx, SIV Vpr and SIV Vpx, and wherein said viral protein sequence is selected from the group consisting of SEQ ID NO:1, SEQ ID NO:2, SEQ ID NO:3, and SEQ ID NO:4, wherein said recombinant protein interacts with said p6 domain of said viral particle when said recombinant is expressed in trans with respect to the genome of said viral particle, thereby enabling the incorporation of said recombinant protein into said viral particle.

8. The method of claim 7, wherein said viral protein sequence is selected from the group consisting of:

i) amino acids 1–72 of SEQ ID NO:1 of HIV-1 Vpr;

ii) amino acids 1–88 of SEQ ID NO:1 of HIV-1 Vpr; and iii) amino acids 1–93 of SEQ ID NO:1 of HIV-1 Vpr.

9. A method for incorporating a chimeric protein into a viral particle when expressed in trans with respect to the genome thereof, comprising interacting said chimeric protein in a viral particle packaging cell line with the p6 domain of a Pr55gag precursor protein present in said viral particle packaging cell line, said chimeric protein having a first and second portion, wherein said first portion has a Vpr/Vpx virion incorporation domain which includes the predicted N-terminal alpha helix of a viral protein selected from the group consisting of HIV-1 Vpr, HIV-2 Vpr, HIV-2 Vpx, SIV Vpr and SIV Vpx, wherein said first portion consists of an amino acid sequence selected from the group consisting of amino acids 1 to 88 of SEQ ID NO:1, and amino acids 1 to 72 of SEQ ID NO:1;

wherein the interaction of said Vpr/Vpx virion incorporation domain of said chimeric protein with said p8 domain of Pr55gag in said viral particle, enables the incorporation of said chimeric protein into said viral particle.

10. A method for incorporating a chimeric protein into a viral particle when expressed in trans with respect to the genome thereof, comprising interacting said chimeric protein in a viral particle packaging cell line with the p6 domain of a Pr55gag precursor protein present in said viral particle packaging cell line, said chimeric protein having a first and second portion, wherein said first portion has a Vpr/Vpx virion incorporation domain which includes the predicted N-terminal alpha helix of a viral protein selected from the group consisting of HIV-1 Vpr, HIV-2 Vpr, HIV-2 Vpx, SIV Vpr and SIV Vpx;

wherein said second portion interferes with protein interactions necessary for formation or infectivity of HIV-1 or HIV-2 virion; and wherein the interaction of said Vpr/Vpx virion incorporation domain of said chimeric protein with said p6 domain of Pr55gag in said viral particle enables the incorporation of said chimeric protein in said viral particle.

11. A method for incorporating a chimeric protein into a virion comprising interacting said chimeric protein in trans with respect to the genome of said virion, said chimeric protein comprising a first and second portion, wherein said first portion has a Vpr/Vpx virion incorporation domain which includes the predicted N-terminal alpha helix of the viral protein selected from the group consisting of HIV-1 Vpr, HIV-2 Vpr, HIV-2 Vpx, SIV Vpr and SIV Vpx and said second portion is fused to the C-terminal portion of said first portion; and wherein said virion contains the p6 domain of a Pr55gag precursor protein;

wherein the interaction of said Vpr/Vpx virion incorporation domain of said chimeric protein with said p6 domain of Pr55gag of the virion, enables the incorporation of said chimeric protein into said virion.

* * * * *